United States Patent

Ishikawa et al.

[11] Patent Number: 5,906,208
[45] Date of Patent: May 25, 1999

[54] METHOD AND APPARATUS FOR JUDGING A DEPTH OF ANESTHESIA

[75] Inventors: Norio Ishikawa; Kohei Ono; Katsumi Nakaichi; Shin Suda; Hidehiro Hosaka; Ryoichi Ochiai, all of Tokyo, Japan

[73] Assignee: Nihon Kohden Corporation, Tokyo, Japan

[21] Appl. No.: 08/832,797

[22] Filed: Apr. 4, 1997

[30] Foreign Application Priority Data

Apr. 5, 1996 [JP] Japan ................................. 8-083887

[51] Int. Cl.$^6$ ........................... A61M 15/00; A61B 19/00
[52] U.S. Cl. .................. 128/898; 128/200.24; 600/300; 600/306; 600/547
[58] Field of Search .................... 600/300, 306, 600/301, 547, 544; 128/200.24, 897, 898

[56] References Cited

U.S. PATENT DOCUMENTS

| | | | |
|---|---|---|---|
| 3,513,834 | 5/1970 | Suzuki et al. | 600/544 |
| 4,533,346 | 8/1985 | Cosgrove, Jr. et al. | 600/544 |
| 4,545,388 | 10/1985 | John | 600/544 |
| 4,739,772 | 4/1988 | Hokanson et al. | 600/544 |
| 4,846,190 | 7/1989 | John | 600/544 |
| 4,869,264 | 9/1989 | Silberstein | 600/544 |
| 4,880,014 | 11/1989 | Zarowitz et al. | 600/547 |
| 4,907,597 | 3/1990 | Chamoun | 600/544 |
| 4,928,090 | 5/1990 | Yoshimi et al. | |
| 5,010,891 | 4/1991 | Chamoun | 600/544 |
| 5,320,109 | 6/1994 | Chamoun et al. | 600/544 |
| 5,370,126 | 12/1994 | Clifford, Jr. | 600/544 |
| 5,458,117 | 10/1995 | Chamoun et al. | 600/547 |
| 5,699,808 | 12/1997 | John | 600/544 |
| 5,730,146 | 3/1998 | Itil et al. | 600/544 |

FOREIGN PATENT DOCUMENTS 091019453 12/1991 WIPO ................................. 600/544

OTHER PUBLICATIONS

Ochiai, Tada, et al., 110 Changes In Skin Potential level During inhalation Anesthesia, published Sep. 30, 1995, (p. 83, right column) in The 35$^{th}$ Japan Society of Anesthesiology (Partially Translated).

*Primary Examiner*—Mickey Yu
*Assistant Examiner*—Dinh X. Nguyen
*Attorney, Agent, or Firm*—Sughrue, Mion, Zinn, Macpeak & Seas, PLLC

[57] ABSTRACT

The apparatus has: electrodes ($E_1$ to $E_6$) which are to be attached to a predetermined region of a living body; a skin potential measuring unit (1) which detects the skin potential from the electrodes; a judging unit (3) which detects and stores the skin potential before administration of an anesthetic agent, which detects and stores that after administration of the anesthetic agent, which sets a threshold to be an arbitrary level, on the basis of a change from the stored skin potential before administration of the anesthetic agent to the stored skin potential after administration of the anesthetic agent, and which compares the time-varying skin potential with the threshold, thereby judging the depth of anesthesia; and an alarm unit (6) which raises an alarm in accordance with instructions from the judging unit.

5 Claims, 3 Drawing Sheets

METHOD AND APPARATUS FOR JUDGING A DEPTH OF ANESTHESIA

BACKGROUND OF THE INVENTION

1. Field of the Invention

The invention relates to a method and an apparatus for judging a depth of anesthesia and raising an alarm.

2. Related Art

When a patient in sickness is to undergo an operation or a test, anesthesia is previously given to the patient. Conventionally, there is no apparatus which can correctly measure or judge the depth of anesthesia. In fact, after anesthesia is given to the patient, therefore, the doctor measures parameters such as the blood pressure, and the respiration and empirically presumes the depth of anesthesia, and thereafter the patient undergoes the operation or the test.

From the standpoint of the patient, the judgement whether the depth of anesthesia is sufficient or not is important. When the depth of anesthesia is sufficient in general anesthesia, for example, the patient is unconscious and does not feel a pain due to incision by using a knife. Therefore, the patient cannot hear discussions between the doctor and the nurse, so that the patient does not feel apprehension about the discussions and their movement.

By contrast, when the depth of anesthesia is insufficient, the patient feels pain in the incision region, or the patient is conscious. Under this state, since the patient is conscious, the patient feels apprehension about the operation. During the operation, particularly, the patient is in the state where the patient cannot move and utter, and hence cannot tell the doctor or the nurse that the anesthesia is insufficient. It seems that, since the patient is conscious, the patient feels even fear under the state where the patient is very sensitive to surrounding discussions and movement of the doctor and the nurse engaging, in the operation. An instance in which an operation was carried out while the depth of anesthesia was insufficient and the patient was conscious has been reported.

Recently, in order to reduce the effect of administration of an anesthetic agent on a living body, there is a tendency to perform an operation with administration of an anesthetic agent of the minimum level. Consequently, an apparatus or a method which can correctly judge a depth of anesthesia will play an important role, and hence it is requested to early develop such an apparatus or a method.

As described above, however, an apparatus which can correctly measure or judge the depth of anesthesia in administration of an anesthetic agent is not available at present.

SUMMARY OF THE INVENTION

The invention has been conducted in view of the problem discussed above. It is an object of the invention to provide a method and an apparatus for judging a depth of anesthesia in which the depth of anesthesia is judged by measuring a skin potential and setting a threshold, and, when the depth of anesthesia is insufficient, an alarm is raised.

In the method of judging a depth of anesthesia depth of the invention, a skin potential is detected from a predetermined region of a living body, a skin potential before administration of an anesthetic agent is detected and stored, a skin potential after administration of the anesthetic agent is detected and stored, a threshold is set to be an arbitrary level, on the basis of a change from the stored skin potential before administration of the anesthetic agent to the stored skin potential after administration of the anesthetic agent, the time-varying skin potential is compared with the threshold, thereby judging a depth of anesthesia, and an alarm is raised on the basis of a result of the judgement.

Figure 1:
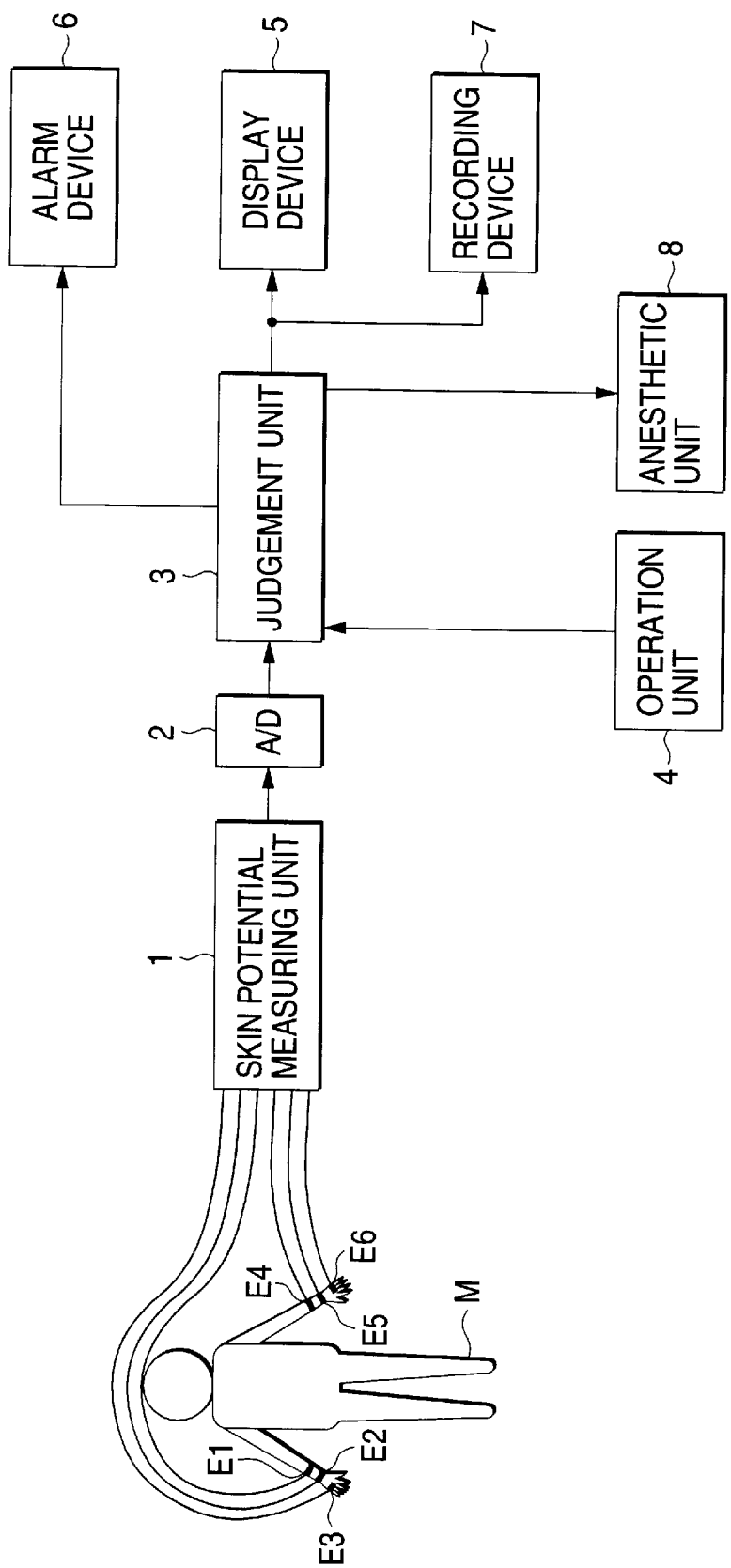
FIG. 1 is a block diagram showing the configuration of an embodiment of an apparatus which is used in the method of judging a depth of anesthesia of the invention.

The apparatus for judging a depth of anesthesia of the invention includes: as shown in, for example, FIG. 1, several electrodes which are to be attached to a predetermined region of a living body; a skin potential measuring unit which detects a skin potential from the electrode; a judging unit which detects and stores a skin potential before administration of an anesthetic agent, which detects and stores a skin potential after administration of the anesthetic agent, which sets a threshold to be an arbitrary level, on the basis of a change from the stored skin potential before administration of the anesthetic agent to the stored skin potential after administration of the anesthetic agent, and which compares the time-varying skin potential with the threshold, thereby judging a depth of anesthesia; and an alarm unit which raises an alarm in accordance with instructions from the judging unit.

According to the present invention, a skin potential is detected from a predetermined region of a living body, and skin potentials before administration of an anesthetic agent and after administration of the anesthetic agent are detected and stored. A threshold is set to be an arbitrary level in a change from the stored skin potential before administration of the anesthetic agent to the stored skin potential after administration of the anesthetic agent. The time-varying skin potential is compared with the preset threshold, thereby judging the depth of anesthesia. On the basis of a result of the judgement, an alarm is raised. Therefore, information of the depth of anesthesia of the patient can be obtained easily and surely during an operation or a test.

DETAILED DESCRIPTION OF THE PREFERRED EMBODIMENTS

Figure 2:
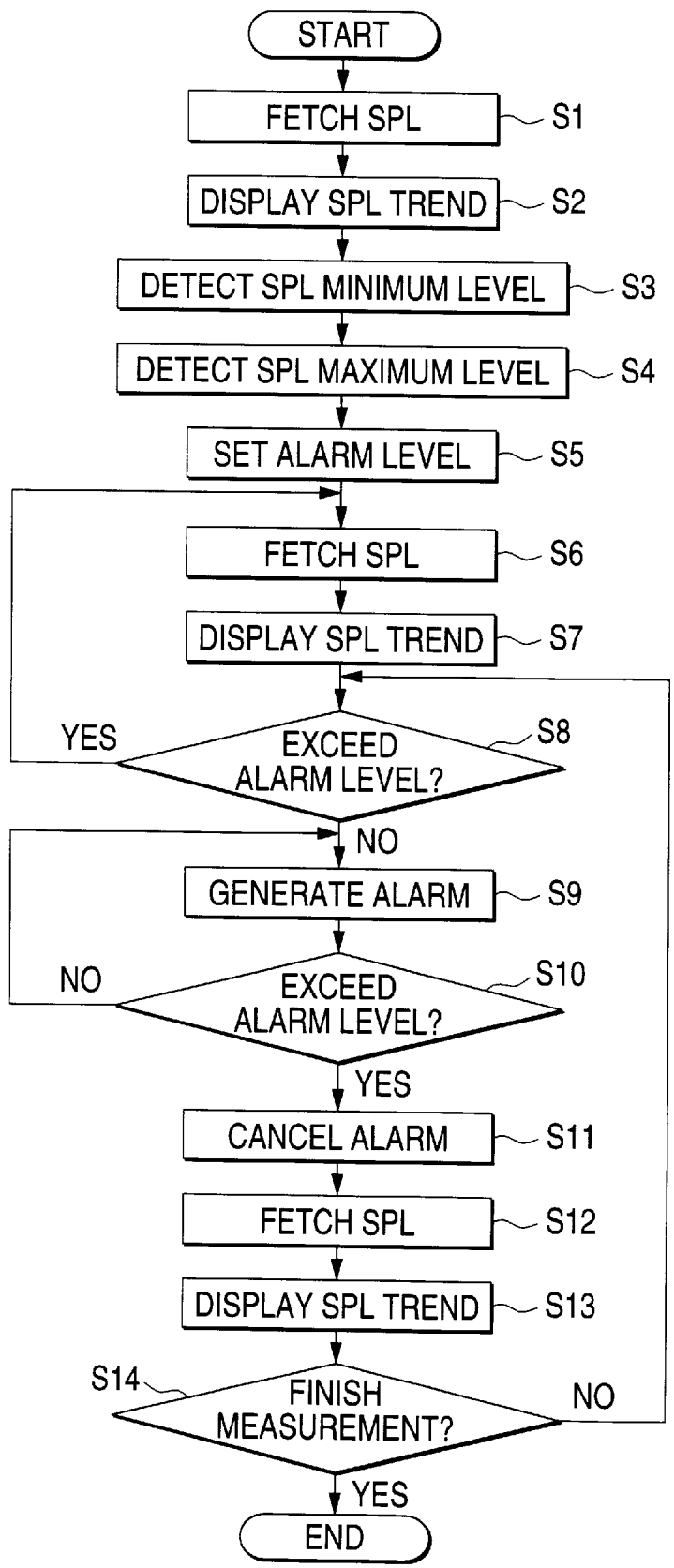
FIG. 2 is a flowchart showing the flow of the judgement of a depth of anesthesia in the embodiment of FIG. 1.
Figure 3:
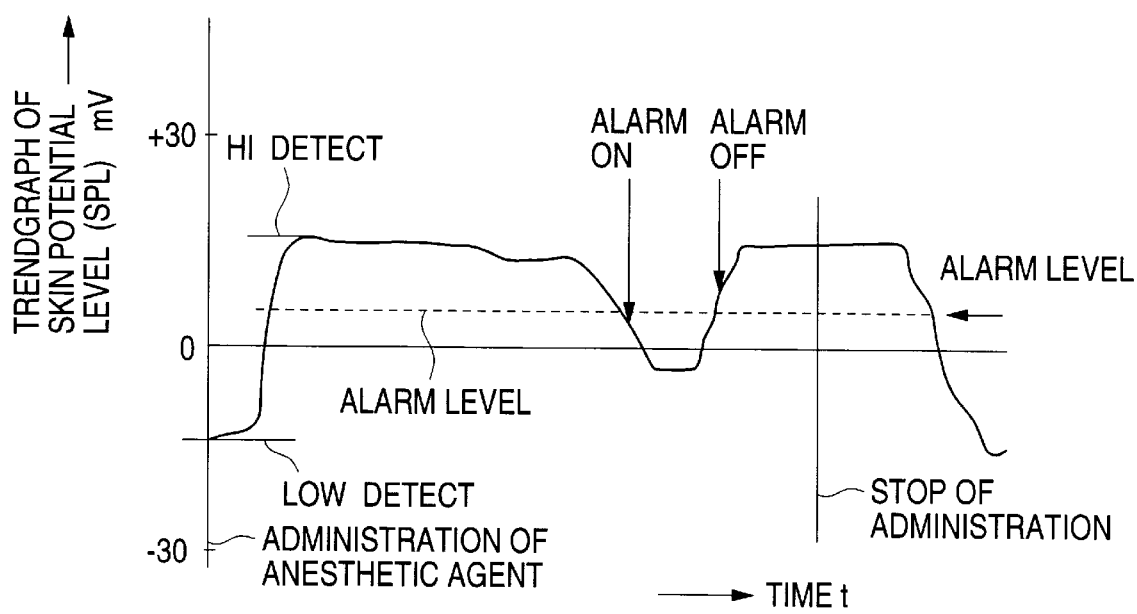
FIG. 3 is a trendgraph of the SPL which is displayed in the embodiment of FIG. 1.

Hereinafter, an embodiment of the method and the apparatus for judging a depth of anesthesia of the invention will be described with reference to the accompanying drawings. FIG. 1 is a block diagram showing the configuration of an embodiment of an apparatus which executes the method of judging a depth of anesthesia of the invention, FIG. 2 is a flowchart showing the flow of the judgement of a depth of anesthesia according to the invention, and FIG. 3 is a view showing a trendgraph of the SPL (Skin Potential Level) during anesthesia which is detected from one hand.

In FIG. 1, 1 designates a skin potential measuring unit which incorporates, for example, a bioamplifier and the like, and which detects skin potential levels (hereinafter, abbreviated as SPLS) lead from electrodes $E_1$ to $E_3$ attached to a predetermined region of a living body, for example, the vicinity of the wrist of the right hand, and electrodes $E_4$ to $E_6$ attached to the vicinity of the wrist of the left hand.

In the illustrated example, the electrodes $E_1$ to $E_3$ are attached to the right hand, and the electrodes $E_4$ to $E_6$ to the left hand. Alternatively, electrodes may be attached only to one hand. In view of a possible accident in which the SPL cannot be detected from one hand because of a drop of an electrode attached to one hand which, may be caused by any reason, higher safety can be attained by attaching electrodes to both hands. When three electrodes are attached to each of the hands as shown in FIG. 1 so that the SPL is obtained by the bipolar lead, there is an advantage that the lead is hardly affected by external noises or the like. Alternatively, the SPL may be detected by means of the monopolar lead in which the center electrode $E_2$ of the left hand is used as an indifferent electrode (reference electrode) and the SPL between the electrodes $E_2$ and $E_3$ is lead, and/or the center electrode $E_5$ of the right hand is used as an indifferent electrode and the SPL between the electrodes $E_5$ and $E_6$ is lead. In the case of the monopolar lead, since the number of electrodes is small, the electrodes can be easily attached and the time period for attachment can be shortened. Therefore, the leading method may be determined to be either of the monopolar lead and the bipolar lead, depending on the environment of the operation or test. Also, it is cosiderable that an indifferent electrode can be positioned at non-body region by making a potential artificially.

The electrodes may be attached to an arbitrary region of a living body. When the positive electrode is attached to a portion where perspiration due to the autonomic nerve is high and the negative electrode to a portion where perspiration is low, particularly, a large potential difference is obtained and hence the judgment can be easily performed. Preferably, such perspiration portions are the palms of the hands and the vicinity of the wrist, or the vicinity of the ankles and the soles of the feet.

The reference numeral 2 designates an analog-digital converter which converts the SPL detected by the skin potential measuring unit 1 into a digital signal and outputs the signal, and 3 designates a judgement unit configured by, for example, a CPU having a RAM and a ROM, and the like. The judgement unit detects the Low level before administration of the anesthetic agent, and the High level after administration of the anesthetic agent, from the SPL measured by the skin potential measuring unit 1, compares the SPL which is sequentially detected with an alarm level which is preset as the threshold, and outputs an alarm signal in accordance with a result of the comparison. The judgement unit conducts also the control of the whole of the apparatus. When the judgement of the depth of anesthesia is to be automatically conducted, programs of judging the depth of anesthesia are previously stored in the ROM, thereby enabling the judgement to be conducted. Alternatively, the judgment may be manually conducted by setting and operating an operation unit 4 which is described below. The RAM temporarily stores data of the Low level of the SPL before administration of the anesthetic agent, those of the High level of the SPL after administration of the anesthetic agent, the alarm level in the case of the manual judgment, and other required data.

The alarm signal is output from the judgement unit 3 when the detected SPL level is lower than the alarm level, i.e., when the depth of anesthesia or the depth of sleep is insufficient.

The reference numeral 4 is the operation unit configured by a keyboard, an operation panel having push bottons, or the like. Through the operation unit, the automatic judgement or the manual judgement is selected, the Low and High levels of the SPL measured by the skin potential measuring unit 1 are set, the alarm level is set, the alarm is canceled, and various required data are set. The reference numeral 5 designates a display device which is configured by, for example, a CRT or a liquid crystal display device, and which displays the trend of the SPL, the alarm level, required data, and the like.

The reference numeral 6 designates an alarm device configured by, for example, a light emitting device such as a light emitting diode (LED), and a driving unit for the light emitting device. In response to the alarm signal output from the judgement unit 3, the alarm device raises an alarm in the form of lighting or blinking. Alternatively, the alarm device 6 may be configured by a sound device such as a buzzer or a small loudspeaker, and a driving unit for the sound device, and raises an alarm in the form of a buzzing sound, a voice, or the like. The alarm device 6 may be configured by combining an LED with either of a buzzer and a loudspeaker so as to simultaneously conduct the alarm operation in the form of light and sound. According to this configuration, the alarm can be surely transmitted to the doctor or the nurse.

The reference numeral 7 designates a recording device which records the trend waveform of the SPL output from the judgement unit 3, and temporal changes of the alarm level, and the like, for the purpose of later analysis. The reference numeral 8 designates an anesthesia machine which, in accordance with instructions of the judgement unit 3, functions so as to administrate the anesthetic agent to the living body M and stop the administration, or increase the concentration of the anesthetic agent.

The process of judging the depth of anesthesia in the above-described configuration will be described with reference to the flowchart of FIG. 2 and the trendgraph of the SPL of FIG. 3. The process of FIG. 2 is conducted when the automatic judgment is selected through the operation unit 4. The trend waveforms of the SPLs obtained from the predetermined regions of the hands are substantially identical with each other. Therefore, the detection of the SPL is conducted by means of the monopolar lead in which two electrodes $E_2$ and $E_3$ are attached to a predetermined region of the right hand. In the trendgraph of the SPL of FIG. 3, the minus side of the ordinate indicates an insufficient depth of anesthesia or an arousal state, and the plus side indicates a sufficient depth of anesthesia or a sufficient depth of sleep. The abscissa indicates the elapsed time.

The SPL is fetched through the electrodes $E_2$ and $E_3$, the skin potential measuring unit 1, and the analog-digital converter 2 (step S1). The SPL data supplied to the judgement unit 3 are sent to the display device 5 so that the trend waveform of the SPL is displayed on the screen (step S2). As shown in FIG. 3, after administration of the anesthetic agent of concentration of 5%, for example, the value of the detected SPL is rapidly changed from the minus side to the plus side at the timing when the anesthetic agent takes effect. This indicates that the depth of anesthesia or the depth of sleep is sufficient.

From the fetched SPL, the judgement unit 3 detects the Low level before administration of the anesthetic agent, i.e., the SPL of the Low level in an arousal state and stores it (step S3), and further detects the SPL of the High level after administration of the anesthetic agent and stores it (step S4). In this case, for example, a method may be employed in which the SPL before the operation and after a lapse of 30 minutes from the attachment of the electrodes is detected and automatically stored in order to determine the Low level of the SPL, and the SPL after a lapse of 30 minutes from the administration of the anesthetic agent is automatically read from the graph and stored in order to determine the High level of the SPL.

Next, the judgement unit 3 sets the relative changed amount ranging from the Low level of the stored SPL to the High level, to be 100%, and the position which is, for example, at about 60% as counted from the Low level toward the plus side (the broken line in FIG. 3) to be the alarm level (step S5), and continues the measurement of the SPL (step S6). The alarm level can be arbitrarily set by the doctor in consideration of the kind of the anesthetic agent, the scheduled time of the operation, the blood pressure of the patient (before the operation), the conditions of the patient, etc.

The judgement unit 3 monitors the SPL which is sequentially input, and detects whether the depth of anesthesia or the depth of sleep is lower than the alarm level or not (step S8). If the SPL is lower than the alarm level or the depth of anesthesia or the depth of sleep is insufficient, the alarm signal is sent to the alarm device 6 and an alarm in the form of, for example, blinking of light is given by the alarm device 6 (step S9). At the same time, the judgement unit 3 sends the anesthesia machine 8 a signal instructing that, for example, the concentration of the anesthetic agent is increased. When the instruction is recognized, the doctor can increase the concentration of the anesthetic agent, whereby the SPL is again raised so that the depth of anesthesia or the depth of sleep is made sufficient (FIG. 3).

If it is judged in step S8 that the SPL is not lower than the alarm level, the process returns to step S6 to measure the SPL and the display of the trend waveform of the SPL in step S7 is continued.

After the alarm is raised in step S9, the judgement unit 3 again judges whether the SPL is lower than the alarm level or not (step S10). If the SPL is not lower than the alarm level, the operation unit 4 is operated so as to cancel the alarm (step S11), thereby stopping the alarm operation of the alarm device 6. At this time, the anesthesia machine 8 continues the administration of the anesthetic agent while maintaining the anesthetic concentration at this timing.

If it is judged in step S10 that the SPL remains to be lower than the alarm level or the depth of anesthesia or the depth of sleep is insufficient, the process returns to step S9 to continue the alarm operation.

After the alarm operation is ended in step S11, the measurement of the SPL is again started (step S12), and the SPL trend is displayed on the screen of the display device 5 or the recording device 7 records the SPL (step S13).

It is judged whether the measurement is to be continued or not (step S14). If the measurement is not to be continued, the operation of the anesthesia machine 8 is stopped and the measurement is ended. If the measurement is to be continued, the process returns to step S8 to repeat the process subsequent to step S8.

As described above, the process of the flowchart of FIG. 2 is the automatic judgment. Alternatively, the detection of the High and Low levels of the SPL and the setting of the alarm level in steps S3, S4, and S5 of FIG. 3 may be manually conducted while observing the SPL trend displayed on the screen of the display device 5. In the alternative, the doctor or the nurse reads the values of the High and Low levels of the SPL before and after administration of the anesthetic agent, from the display of the trend on the screen, and inputs the numerical data of the levels and also the alarm level through the keys of the operation unit 4. In this case, the change ranging from the Low level to the High level of the SPL displayed on the screen of the display device 5 is read, the change is set to be 100%, and the position which is, for example, at about 60% as counted from the Low level toward the plus side is set to be the alarm level.

In this way, according to the invention, the depth of anesthesia or the depth of sleep can be judged by either of the automatic and manual operations. Therefore, mental apprehension and physical pain of the patient can be surely eliminated, and the doctor or the nurse can surely know the anesthetic state.

As described above, according to the present invention, the judgement of the depth of anesthesia which cannot be conducted in the prior art can be easily conducted, and it is required only to administrate to the patient an anesthetic agent of the minimum level. Therefore, the effect of administration of an anesthetic agent on the patient can be reduced. Since the doctor or the nurse is informed of the state where the depth of anesthesia is insufficient, the invention has advantages that the doctor or the nurse can surely know the state of the depth of anesthesia, and that an operation or a test is prevented from being performed under the state where the patient is conscious.

What is claimed is:

1. A method of judging a depth of anesthesia comprising:

detecting a pre-anesthesia skin potential from a predetermined region of a living body before administration of an anesthetic agent;

detecting a post-anesthesia skin potential after administration of the anesthetic agent;

setting a threshold level on the basis of at least said pre-anesthesia skin potential;

judging said depth of anesthesia by comparing said post-anesthesia skin potential levels with said threshold level; and activating an alarm on the basis of a result of said judging step.

2. An apparatus for judging a depth of anesthesia, comprising an electrode to be attached to a predetermined region of a living body;

a skin potential measuring unit for detecting a skin potential from said electrode;

a judging unit for detecting a pre-anesthesia skin potential before administration of an anesthetic agent, for detecting a post-anesthesia skin potential after administration of the anesthetic agent, for setting a threshold level on the basis of at least said pre-anesthesia skin potential, and for judging said depth of anesthesia by comparing said post-anesthesia skin potential levels with said threshold level and an alarm unit for activating an alarm in accordance with an output signal from said judging unit.

3. The method according to claim 1, wherein said step of detecting said post-anesthesia skin potential comprises detecting said post-anesthesia skin potential from said predetermined region of the living body after administration of the said anesthetic agent;

wherein said step of setting said threshold level comprises setting said threshold level on the basis of a change from said pre-anesthesia skin potential to said post-anesthesia skin potential after administration of said anesthetic agent; and wherein said step of judging said depth of anesthesia comprises judging said depth of anesthesia by comparing subsequent post-anesthesia skin potential levels with said threshold level.

4. The method according to claim 1, wherein said predetermined region of the living body comprises at least one of a palm of a hand, a position at least proximate to a wrist, a position at least proximate to an ankle, and soles of feet.

5. The apparatus according to claim 2, wherein said judging unit sets said threshold level on the basis of a change from said pre-anesthesia skin potential to said post-anesthesia skin potential after administration of the anesthetic agent, and judges said depth of anesthesia by comparing subsequent post-anesthesia skin potential levels with said threshold level.

* * * * *